(12) United States Patent
Xu et al.

(10) Patent No.: US 7,241,912 B2
(45) Date of Patent: *Jul. 10, 2007

(54) COPPER (I) COMPOUNDS USEFUL AS DEPOSITION PRECURSORS OF COPPER THIN FILMS

(75) Inventors: Chongying Xu, New Milford, CT (US); Alexander Borovik, West Hartford, CT (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/149,045

(22) Filed: Jun. 9, 2005

(65) Prior Publication Data

US 2005/0283012 A1 Dec. 22, 2005

Related U.S. Application Data

(63) Continuation of application No. 10/869,532, filed on Jun. 16, 2004.

(51) Int. Cl.
*C07F 1/08* (2006.01)
*C23C 16/00* (2006.01)
(52) U.S. Cl. ............. 556/110; 427/248.1; 427/255.28; 106/1.26
(58) Field of Classification Search ................ 556/110; 427/248.1, 587, 593, 255.28; 106/1.26
See application file for complete search history.

(56) References Cited

U.S. PATENT DOCUMENTS

| | | |
|---|---|---|
| 5,085,731 A | 2/1992 | Norman et al. |
| 5,098,516 A | 3/1992 | Norman et al. |
| 5,144,049 A | 9/1992 | Norman et al. |
| 5,204,314 A | 4/1993 | Kirlin |
| 5,225,561 A | 7/1993 | Kirlin et al. |
| 5,280,012 A | 1/1994 | Kirlin et al. |
| 5,322,712 A | 6/1994 | Norman et al. |
| 5,362,328 A | 11/1994 | Gardiner et al. |
| 5,453,494 A | 9/1995 | Kirlin et al. |
| 5,536,323 A | 7/1996 | Kirlin et al. |
| 5,711,816 A | 1/1998 | Kirlin et al. |

(Continued)

FOREIGN PATENT DOCUMENTS

DE 4039449 6/1992

(Continued)

OTHER PUBLICATIONS

Van Vliet et al., Journal of Organometallic Chemistry, vol. 179, pp. 89-100 (1979).*

(Continued)

*Primary Examiner*—Porfirio Nazario-Gonzalez
(74) *Attorney, Agent, or Firm*—Steven J. Hultquist; Intellectual Property/Technology Law

(57) ABSTRACT

Copper (I) amidinate precursors for forming copper thin films in the manufacture of semiconductor devices, and a method of depositing the copper (I) amidinate precursors on substrates using chemical vapor deposition or atomic layer deposition processes.

10 Claims, 3 Drawing Sheets

U.S. PATENT DOCUMENTS

| | | | |
|---|---|---|---|
| 5,820,664 | A | 10/1998 | Gardiner et al. |
| 5,919,522 | A | 7/1999 | Baum et al. |
| 5,932,363 | A | 8/1999 | Hu et al. |
| 6,110,529 | A | 8/2000 | Gardiner et al. |
| 6,337,148 | B1 | 1/2002 | Xu et al. |
| 6,417,369 | B1 | 7/2002 | Xu et al. |
| 6,440,202 | B1 | 8/2002 | Xu et al. |
| 6,639,080 | B2 | 10/2003 | Xu et al. |
| 2005/0042372 | A1 | 2/2005 | Denk et al. |

FOREIGN PATENT DOCUMENTS

| | | |
|---|---|---|
| EP | 1142894 | 10/2001 |
| WO | WO 2004/046417 | 6/2004 |

OTHER PUBLICATIONS

Shibayama et al.; Macromolecules, vol. 30, No. 11, pp. 3159-3163 (1997).*

Barker, James, et al., The coordination chemistry of the amidine ligand, Coordination Chemistry Reviews, 1994, pp. 219-300, vol. 133.

Edelmann, Frank T., N-silyated benzamidines: versatile building blocks in main group and coordination chemistry, Coordination Chemistry Reviews, 1994, pp. 403-481, vol. 137.

Cotton, F.A., Feng, X., Matusz, M., Poli, R., *J. Am. Chem. Soc.*, 110, 7077-7083 (1988).

Kilner, M., Pietrzykowski, A., *Polyhedron*, 2(12), 1379-1388 (1983).

Lim, B.S., Rahtu, A., Park, J-S., Gordon, R.G., *Inorg. Chem.*, 42, 7951-7958 (2003).

Dias, H.V.R., Polach, S.A., Wang, Z., *J. Fluorine Chem.*, 103, 163-169 (2000).

Lim, B.S., Tahtu, A., Gordon, R.G., *Nature Materials*, vol. 2, 749-754 (2003).

* cited by examiner

COPPER (I) COMPOUNDS USEFUL AS DEPOSITION PRECURSORS OF COPPER THIN FILMS

CROSS REFERENCE TO RELATED APPLICATION

This is a continuation of U.S. patent application Ser. No. 10/869,532 for "Copper (I) Compounds Useful as Deposition Precursors of Copper Thin Films" filed on Jun. 16, 2004 in the name of Chongying Xu, et al.

FIELD OF THE INVENTION

The present invention relates generally to novel copper (I) amidinates and their synthesis, and to a method for production of copper circuits in microelectronic device structures using the novel copper precursors.

DESCRIPTION OF THE RELATED ART

As a result of its low resistivity, low contact resistance, and ability to enhance device performance through the reduction of RC time delays, copper has emerged as a preferred metal for metallization of very large scale integrated (VLSI) devices. Copper metallization has been adopted by many semiconductor device manufacturers for production of microelectronic chips, thin-film recording heads and packaging components.

Chemical vapor deposition (CVD) of copper provides uniform coverage for the metallization. Atomic layer deposition (ALD), which is a modified CVD process, also provides uniform coverage which is critical for copper seed layers. Liquid CVD precursors and/or solid precursors dissolved into solvents enable direct injection and/or the liquid delivery of precursors into a CVD or ALD vaporizer unit. The accurate and precise delivery rate can be obtained through volumetric metering to achieve reproducibility during CVD or ALD metallization of a VLSI device.

Many fluorine and/or oxygen-containing copper CVD precursors are commercially available, including (hfac)Cu (MHY), (hfac)Cu(3-hexyne), (hfac)Cu(DMCOD) and (hfac)Cu(VTMS), wherein hfac=1,1,1,5,5,5-hexafluoroacetylacetonato, MHY=2-methyl-1-hexen-3-yne, DMCOD=dimethylcyclooctadiene, and VTMS=vinyltrimethylsilane.

Copper metallization in integrated circuit manufacture typically utilizes a barrier layer between the copper layer and the underlying structure in order to prevent detrimental effects that may be caused by the interaction of a copper layer with other portions of the integrated circuit. A wide range of barrier materials is conventionally utilized, including materials comprising metals, metal nitrides, metal silicides, and metal silicon nitrides. Exemplary barrier materials include titanium nitride, titanium silicide, tantalum nitride, tantalum silicide, tantalum silicon nitrides, niobium nitrides, niobium silicon nitrides, tungsten nitride, and tungsten silicide. In instances where (hfac)CuL type precursors are used for copper metallization, interfacial layers are formed between the barrier layer and the copper layer, which cause the metallization to have poor adhesion and high contact resistivity.

The deficiencies of inferior adhesion and excessively high contact resistivity incident to formation of oxygen- and/or fluorine-containing interfacial layers when using (hfac)CuL copper precursors has been attributed to the hfac ligand, which contains both oxygen and fluorine. To overcome such deficiencies, it would be a significant advance in the art to provide copper precursors having a reduced oxy/fluoro content. It would be particularly advantageous to provide copper precursors of an oxygen-free character.

It is accordingly an object of the present invention to provide new anoxic (oxygen-free and fluorine-free) copper precursors and formulations, as well as methods of forming copper in the manufacturing of integrated circuits and other microelectronic device structures using such precursors and formulations.

SUMMARY OF THE INVENTION

The present invention relates generally to copper (I) amidinate compounds, which are advantageously of an oxygen-free and fluorine-free character, useful as source reagents for forming copper on substrates with improved adhesion, and to methods of using such copper (I) amidinate compounds.

The present invention in one aspect relates to a copper precursor compound of the formula:

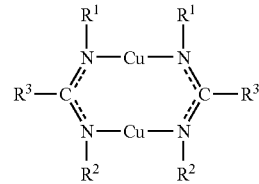

wherein:
$R^1$ and $R^2$ may be the same as or different from one another and each is independently selected from the group consisting of H, $C_1$–$C_6$ alkyl, $C_3$–$C_7$ cycloalkyl, aryl, and hydrocarbyl derivatives of silyl groups (e.g., —$SiR_3$, wherein R is independently selected from the group consisting of $C_1$–$C_6$ alkyl);
$R^3$ is selected from the group consisting of H, $C_1$–$C_6$ alkyl, $C_3$–$C_7$ cycloalkyl, aryl, hydrocarbyl derivatives of silyl groups and $NR^4R^5$, where $R^4$ and $R^5$ may be the same as or different from one another and is independently selected from the group consisting of H, $C_1$–$C_6$ alkyl, $C_3$–$C_7$ cycloalkyl, aryl, and hydrocarbyl derivatives of silyl groups;

with the proviso that when $R^1$ and $R^2$ are isopropyl groups, $R^3$ is not a methyl group.

In another aspect, the present invention relates to a copper precursor formulation, comprising:
(a) a copper precursor compound of the formula:

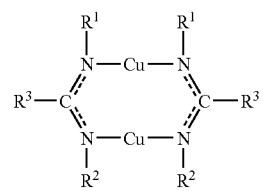

wherein:
$R^1$ and $R^2$ may be the same as or different from one another and each is independently selected from the group consisting of H, $C_1$–$C_6$ alkyl, $C_3$–$C_7$ cycloalkyl, aryl, and hydrocarbyl derivatives of silyl groups;
$R^3$ is selected from the group consisting of H, $C_1$–$C_6$ alkyl, $C_3$–$C_7$ cycloalkyl, aryl, hydrocarbyl derivatives of silyl groups and NR⁴R⁵, where $R^4$ and $R^5$ may be the same as or different from one another and is independently selected from the group consisting of H, $C_1$–$C_6$ alkyl, $C_3$–$C_7$ cycloalkyl, aryl, and hydrocarbyl derivatives of silyl groups;

(b) a solvent composition for the precursor compound.

In yet another aspect, the present invention relates to a method of depositing copper on a substrate, comprising volatilizing a copper precursor of the formula:

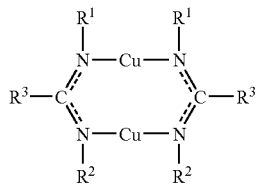

wherein:

$R^1$ and $R^2$ may be the same as or different from one another and each is independently selected from the group consisting of H, $C_1$–$C_6$ alkyl, $C_3$–$C_7$ cycloalkyl, aryl, and hydrocarbyl derivatives of silyl groups;

$R^3$ is selected from the group consisting of H, $C_1$–$C_6$ alkyl, $C_3$–$C_7$ cycloalkyl, aryl, hydrocarbyl derivatives of silyl groups and NR⁴R⁵, where $R^4$ and $R^5$ may be the same as or different from one another and is independently selected from the group consisting of H, $C_1$–$C_6$ alkyl, $C_3$–$C_7$ cycloalkyl, aryl, and hydrocarbyl derivatives of silyl groups;

with the proviso that when $R^1$ and $R^2$ are isopropyl groups, $R^3$ is not a methyl group, to form a precursor vapor and contacting the precursor vapor with the substrate under elevated temperature vapor decomposition conditions to deposit copper on the substrate.

Other aspects, features and embodiments of the invention will be more fully apparent from the ensuing disclosure and appended claims.

DETAILED DESCRIPTION OF THE INVENTION AND PREFERRED EMBODIMENTS THEREOF

Figure 1:
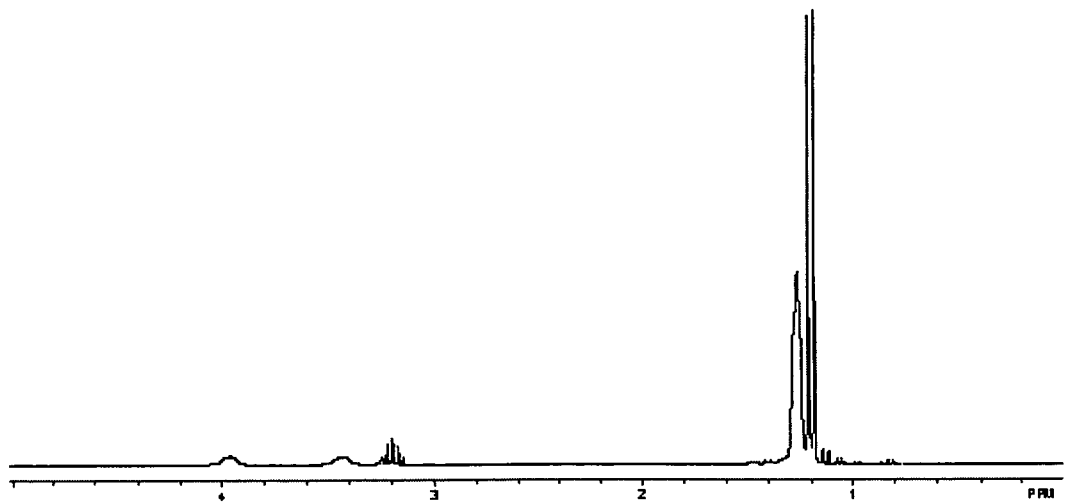
FIG. 1 is an ¹H-NMR plot for copper (I) 2-isopropyl-1,3-diisopropylamidinate.

The present invention relates to novel copper (I) amidinate precursors for the CVD or ALD formation of copper thin films on substrates, and to corresponding processes for using such precursors.

Amidinates are bulky monoanionic ligands which have the basic chemical structure:

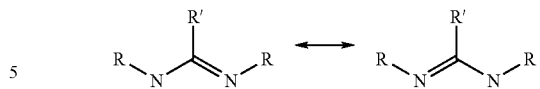

In one aspect, the invention provides a compound of the formula:

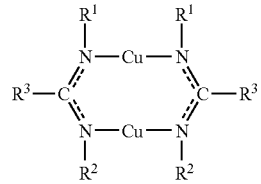

(1)

wherein:

$R^1$ and $R^2$ may be the same as or different from one another and each is independently selected from the group consisting of H, $C_1$–$C_6$ alkyl, $C_3$–$C_7$ cycloalkyl aryl, and hydrocarbyl derivatives of silyl groups (e.g., —SiR₃, wherein R is independently selected from the group consisting of $C_1$–$C_6$ alkyl);

$R^3$ is selected from the group consisting of H, $C_1$–$C_6$ alkyl, $C_3$–$C_7$ cycloalkyl, aryl, hydrocarbyl derivatives of silyl groups and NR⁴R⁵, where $R^4$ and $R^5$ may be the same as or different from one another and is independently selected from the group consisting of H, $C_1$–$C_6$ alkyl, $C_3$–$C_7$ cycloalkyl, aryl, and hydrocarbyl derivatives of silyl groups;

with the proviso that when $R^1$ and $R^2$ are isopropyl groups, $R^3$ is not a methyl group.

The compounds of formula (1) are usefully employed for forming copper thin films by CVD or ALD processes, utilizing process conditions, including appertaining temperatures, pressures, concentrations, flow rates and CVD techniques, as readily determinable within the skill of the art for a given application.

Preferred compounds of formula (1) include copper (I) 2-isopropyl-1,3-diisopropylamidinate:

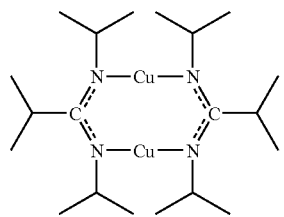

and copper (I) 2-dimethylamino-1,3-diisopropylamidinate:

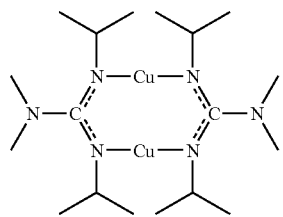

Compounds of formula (I) are readily synthesized according to the following equations (2) and (3):

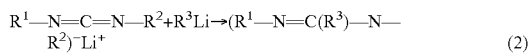

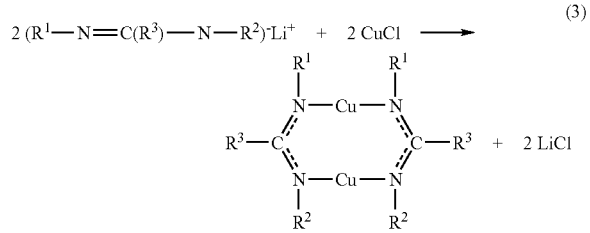

as hereinafter more fully described in the examples herein.

In CVD or ALD usage, the copper (I) precursors of the invention are volatilized to form a precursor vapor that is then contacted with a substrate under elevated temperature vapor decomposition conditions to deposit copper on the substrate.

Copper (I) 2-isopropyl-1,3-diisopropylamidinate and copper (I) 2-dimethylamino-1,3-diisopropylamidinate are both volatile and thermally stable, and are usefully employed as copper CVD or ALD precursors under reducing ambient deposition conditions in the CVD or ALD reactor. The solid precursor can be dissolved in organic solvents, and liquid delivery can be used to meter the solution into a vaporizer for transport to the reactor.

More specifically, and by way of example, the copper (I) amidinate precursor compositions of the present invention may be used during the formation of copper interconnect lines in semiconductor integrated circuitry, thin-film circuitry, thin-film packaging components and thin-film recording head coils. To form such integrated circuitry or thin-film circuitry, a semiconductor substrate may be utilized having a number of dielectric and conductive layers (multilayers) formed on and/or within the substrate. The semiconductor substrate may include a bare substrate or any number of constituent layers formed on a bare substrate.

In the broad practice of the present invention, a copper-containing layer may be formed on a semiconductor substrate using the copper (I) amidinate precursor, for use in a first, second, third, or more metallization layer. Such copper layers typically are used in circuit locations requiring low resistivity, high performance and/or high speed circuit paths. As discussed in the background section hereof, a barrier layer may be deposited or otherwise formed on the substrate before a copper layer is formed on a semiconductor substrate.

Using the copper precursor compositions described herein, copper may then be deposited on the wafer using a CVD or ALD system, such systems being well known in the semiconductor fabrication art. Further, water, water-generating compounds, or other adjuvants to the precursor formulation may be mixed with the copper precursor upstream of, or within, the CVD or ALD tool. Similarly, reducing agents may be utilized in an analogous fashion.

As a further variation, when copper alloy compositions are to be deposited on the substrate, the copper precursor formulation may contain or be mixed with other metal source reagent materials, or such other reagent materials may be separately vaporized and introduced to the deposition chamber.

The compositions of the present invention may be delivered to a CVD or ALD reactor in a variety of ways. For example, a liquid delivery system may be utilized. Alternatively, a combined liquid delivery and flash vaporization process unit may be employed, such as the LDS300 liquid delivery and vaporizer unit (commercially available from Advanced Technology Materials, Inc., Danbury, Conn.), to enable low volatility materials to be volumetrically delivered, leading to reproducible transport and deposition without thermal decomposition of the precursor. Both of these considerations of reproducible transport and deposition without thermal decomposition are essential for providing a commercially acceptable copper CVD or ALD process.

In liquid delivery formulations, copper precursors that are liquids may be used in neat liquid form, or liquid or solid copper precursors may be employed in solvent formulations containing same. Thus, copper precursor formulations of the invention may include solvent component(s) of suitable character as may be desirable and advantageous in a given end use application to form copper on a substrate. Suitable solvents may for example include alkane solvents, e.g., hexane, heptane, octane, pentane, or aryl solvents such as benzene or toluene, amines and amides. The utility of specific solvent compositions for particular copper precursors may be readily empirically determined, to select an appropriate single component or multiple component solvent medium for the liquid delivery vaporization and transport of the specific copper precursor employed.

In another embodiment of the invention, a solid delivery system may be utilized, for example, using the ProE-Vap solid delivery and vaporizer unit (commercially available from Advanced Technology Materials, Inc., Danbury, Conn.).

A wide variety of CVD or ALD process conditions may be utilized with the precursor compositions of the present invention. Generalized process conditions may include substrate temperature ranges of 150–400° C.; pressure ranges of 0.05–5 Torr; and carrier gas flows of helium, hydrogen, nitrogen, or argon at 25–750 sccm at a temperature approximately the same as the vaporizer of 50 to 120° C.

The deposition of copper thin films with useful electrical properties (low resistivity) and good adhesion to the barrier layer (e.g., formed of TiN or TaN), are also achieved by the process and precursors of the present invention. The conformality of the deposited film is practically achievable through CVD or ALD techniques that preferably provide a pathway to the achievement of "full-fill" copper metallization. The liquid delivery approach of the present invention, including "flash" vaporization and the use of copper precursor chemistry as herein disclosed, enable next-generation device geometries and dimensions to be attained, e.g., a conformal vertical interconnect of 65 nanometer linewidths. The conformal deposition of interconnects of these critical dimensions cannot be realized by currently available physical deposition methods. Thus, the approach of the present invention affords a viable pathway to future generation devices, and embodies a substantial advance in the art.

The features and advantages of the invention are more fully shown by the following illustrative and non-limiting examples.

EXAMPLE 1

Synthesis of copper (I) 2-isopropyl-1,3-diisopropylamidinate

The reaction was carried out under a steady flow of nitrogen. A Schlenk flask was charged with 6.3 g of 1,3-diisopropylcarbodiimide ($(CH_3)_2CHN=C=NCH(CH_3)$, 49.9 mmol) and 50 mL dry ether and placed in an ice bath. Then, 32 mL of isopropyllithium (1.6M in ether, 51.2 mmol) was added dropwise to the magnetically stirred mixture at about 0° C. After the addition was complete, the mixture was stirred at room temperature for two additional hours. The mixture was transferred to another flask containing 6 g of CuCl (60.6 mmol) suspended in 50 mL ether. This mixture was stirred at room temperature overnight and then stripped to dryness. The solid residue was extracted with pentane (3×50 mL). After extraction, the pentane filtrate was concentrated to slightly cloudy. The saturated solution was placed in a freezer at −39° C., and crystalline product was obtained in a yield of about 60%.

FIG. 1 shows the $^1$H NMR ($C_6D_6$) for copper (I) 2-isopropyl-1,3-diisopropylamidinate, having the following peaks: δ 1.20 (d, 6H, $(CH_3)_2CH-C$), 1.23 (br, 12H, $(CH_3)_2CH-N$), 3.20 (hept, 1H, CH), 3.45 (br, 1H, CH), 3.95 (br, 1H, CH).

Figure 2:
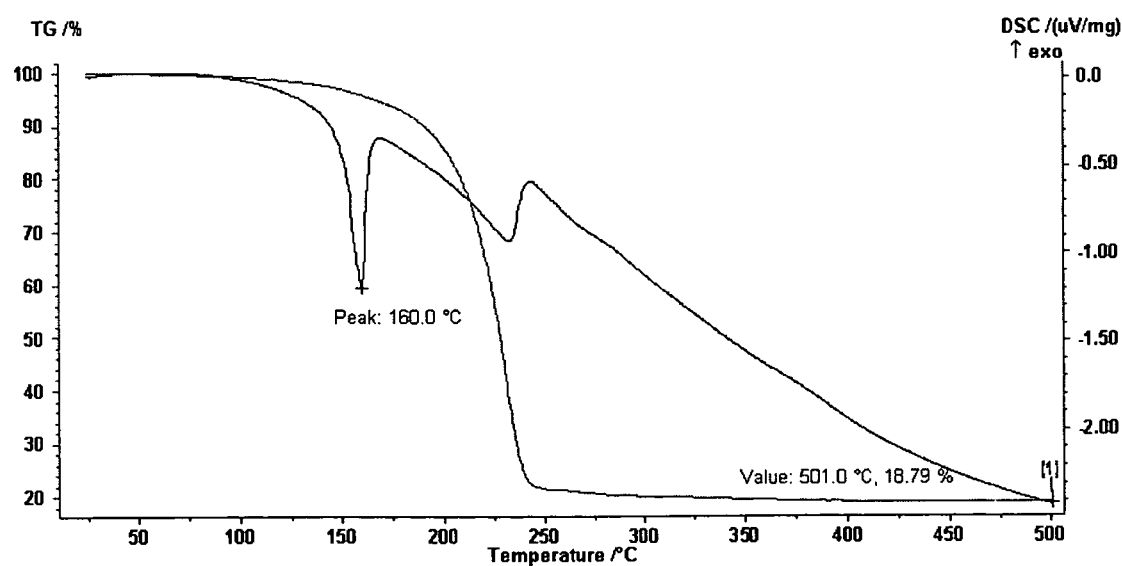
FIG. 2 is a simultaneous thermal analysis (STA)/differential scanning calorimetry (DSC) plot for copper (I) 2-isopropyl-1,3-diisopropylamidinate.

FIG. 2 shows the STA/DSC plot for copper (I) 2-isopropyl-1,3-diisopropylamidinate. The melting peak is about 160° C. and the residue is about 19%.

Figure 3:
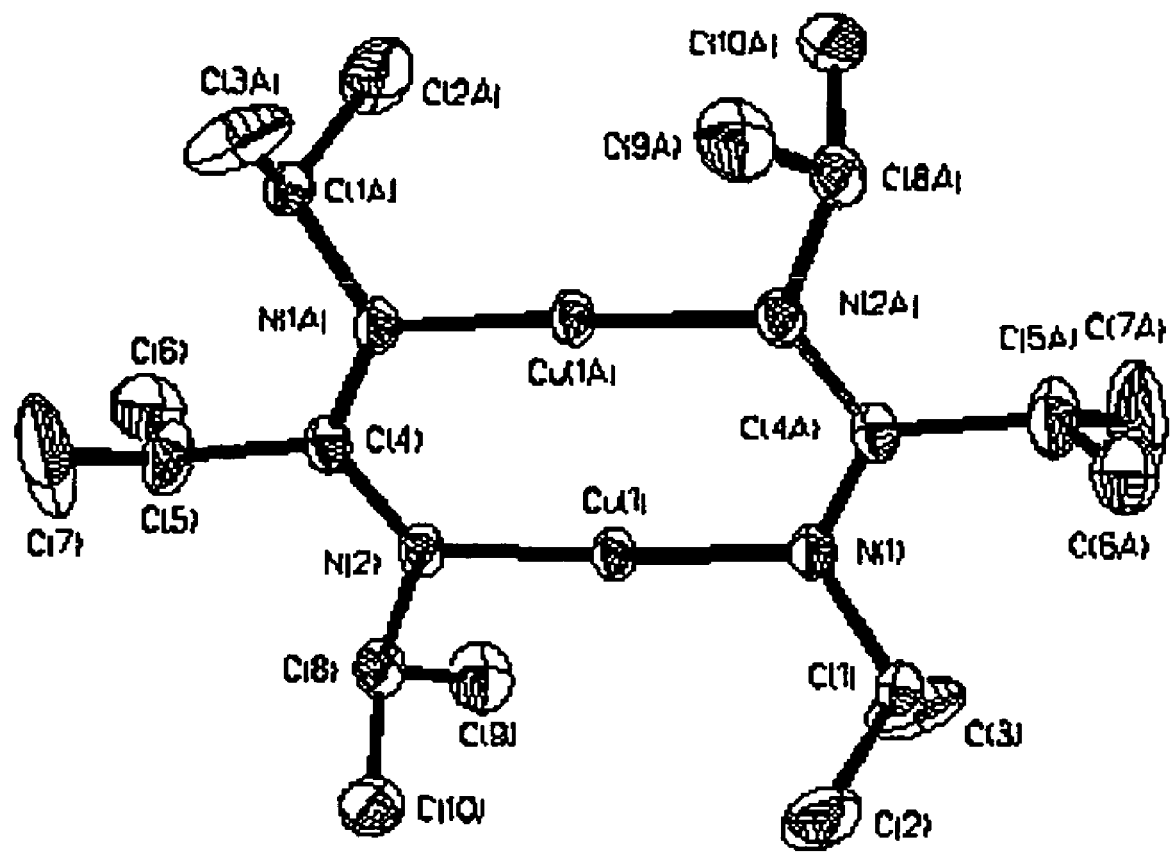
FIG. 3 is an ORTEP structure for copper (I) 2-isopropyl-1,3-diisopropylamidinate.

FIG. 3 is the ORTEP structure for copper (I) 2-isopropyl-1,3-diisopropylamidinate, showing the dimeric structure of the compound and 30% probability thermal ellipsoids.

EXAMPLE 2

Synthesis of copper (I) 2-dimethylamino-1,3-diisopropylamidinate

Neat 1,3-diisopropylcarbodiimide (12.37 g, 98 mmol, 15.2 mL) was slowly added to a solution of $LiNMe_2$ (5 g, 98 mmol) in 125 mL of THF. Some heat generation was observed. The reaction mixture was stirred for 1 hour. Thereafter, 9.7 g of solid CuCl (98 mmol) was added to the reaction mixture in a dry box. The resulting greenish suspension was stirred overnight and all volatiles were removed in vacuum. The residue was washed in 150 mL of hexane. Filtrate was concentrated in vacuum and placed in a refrigerator whereby neat crystals grew overnight. The overall yield was 60% and the melting point of the crystals was 108° C. $^1$H NMR ($C_6D_6$): δ 3.42 (septet, 1H, J(H—H)=6 Hz, $CH(CH_3)_2$), 2.55 (singlet, 3H, $N(CH_3)_2$), 1.30 (doublet, 6H, J(H—H)=6 Hz, $CH(CH_3)_2$). $^{13}$C NMR ($C_6D_6$): δ 171.95 ($Me_2NC(N(iPr))_2$), 48.61 ($CH(CH_3)_2$), 41.29 ($N(CH_3)_2$), 27.98 ($CH(CH_3)_2$).

Figure 4:
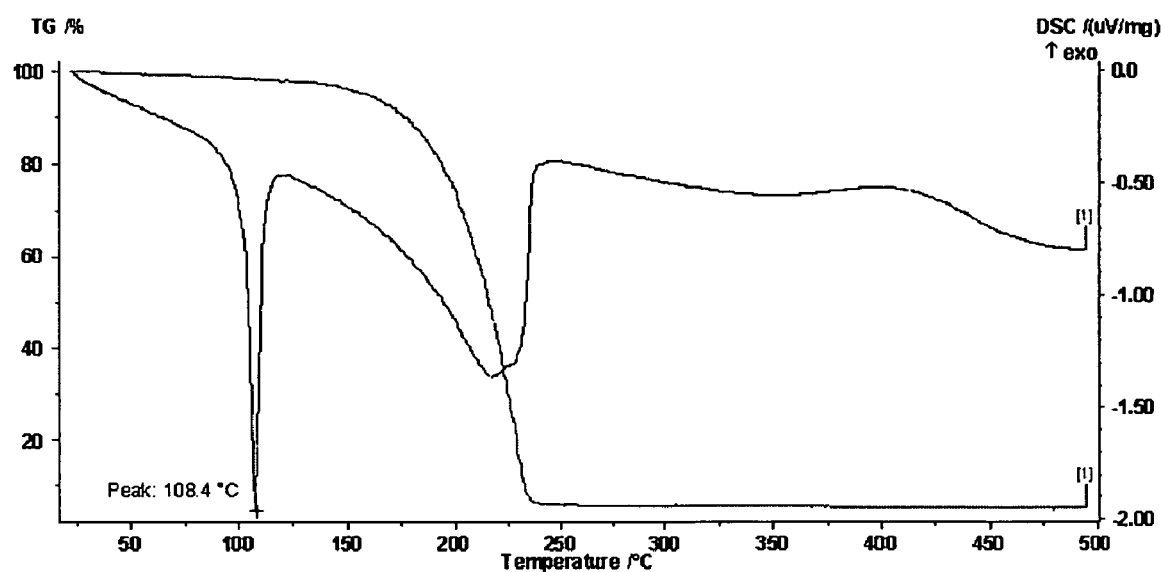
FIG. 4 is an STA/DSC plot for copper (I) 2-dimethylamino-1,3-diisopropylamidinate.

FIG. 4 shows the STA/DSC plot for copper (I) 2-dimethylamino-1,3-diisopropylamidinate, which is volatile with the transport temperature below 230° C., and having a residual mass below 5%.

Figure 5:
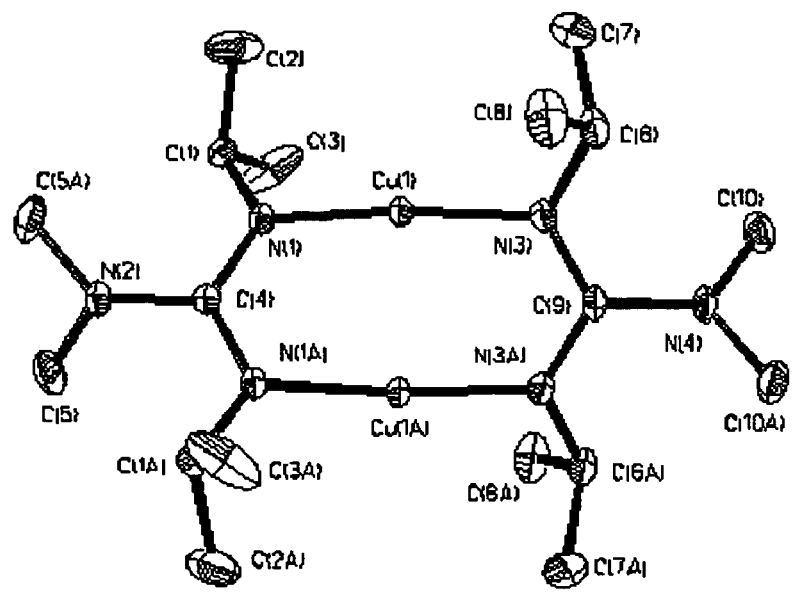
FIG. 5 is an ORTEP structure for copper (I) 2-dimethylamino-1,3-diisopropylamidinate.

FIG. 5 is the ORTEP structure for copper (I) 2-dimethylamino-1,3-diisopropylamidinate, showing the dimeric structure of the compound in the solid state. A relatively short Cu—Cu distance of 2.4152(17) Å may indicate a weak metal-metal interaction. The average Cu—N distance is 1.875(3) Å, which is quite similar to that observed in analogous compounds.

While the invention has been described herein with reference to various specific embodiments, it will be appreciated that the invention is not thus limited, and extends to and encompasses various other modifications and embodiments, as will be appreciated by those ordinarily skilled in the art. Accordingly, the invention is intended to be broadly construed and interpreted, in accordance with the ensuing claims.

What is claimed is:

1. A copper precursor compound of the formula:

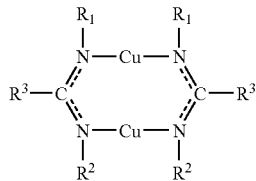

wherein:

$R^1$ and $R^2$ may be the same as or different from one another and each is independently selected from the group consisting of H, $C_1$–$C_6$ alkyl, $C_3$–$C_7$ cycloalkyl, aryl, and hydrocarbyl derivatives of silyl groups;

$R^3$ is selected from the group consisting of H, $C_1$–$C_6$ alkyl, $C_3$–$C_7$ cycloalkyl, aryl, hydrocarbyl derivatives of silyl groups and $NR^4R^5$, where $R^4$ and $R^5$ may be the same as or different from one another and is independently selected from the group consisting of H, $C_1$–$C_6$ alkyl, $C_3$–$C_7$ cycloalkyl, aryl, and hydrocarbyl derivatives of silyl groups;

with the provisos that:

$R^1=R^2\ne$butylphenyl when $R^3$=H;

$R^1\ne$p-tolyl when $R^2$=alkyl or cyclohexyl, and $R^3$=H;

when $R^1$ and $R^2$ are isopropyl groups or sec-butyl groups, $R^3$ is not a methyl group, when $R^1$ and $R^2$ are p-tolyl groups or hydrogen, $R^3$ is not hydrogen, methyl or phenyl, when $R^1$ and $R^2$ are phenyl groups, $R^3$ is not hydrogen, methyl or phenyl, when $R^1$ and $R^2$ are trimethylsilyl groups, $R^3$ is not phenyl, and when $R^1$ and $R^2$ are t-butyl groups or isopropyl groups, $R^3$ is not hydrogen, wherein said copper precursor compound is synthesized by a chemical synthesis including reactions (1) and (2):

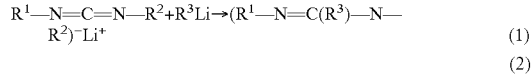

(1)

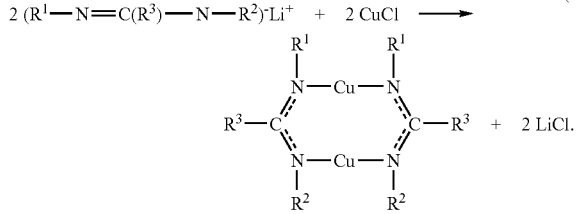

(2)

2. The compound of claim 1, selected from the group consisting of copper (I) 2-isopropyl-1,3-diisopropylamidinate and copper (I) 2-dimethylamine-1,3-diisopropylamidinate.

3. The compound of claim 1, wherein $R^1$ and $R^2$ are isopropyl groups.

4. The compound of claim 1, further comprising a solvent composition for dissolving the copper precursor compound therein.

5. The compound of claim 4, wherein said solvent composition comprises an organic solvent.

6. A copper precursor formulation according to claim 4, wherein said solvent composition comprises a solvent selected from the group consisting of alkane, aryl, amine and amide solvents.

7. A copper precursor formulation according to claim 4, wherein said solvent composition comprises a solvent selected from the group consisting of hexane, heptane, octane, pentane, benzene, toluene, and dimethylformamide.

8. A method of making a copper precursor compound of the formula:

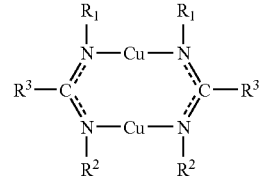

wherein said copper precursor compound is synthesized by a chemical synthesis including reactions (1) and (2):

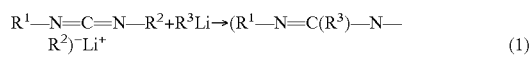

(1)

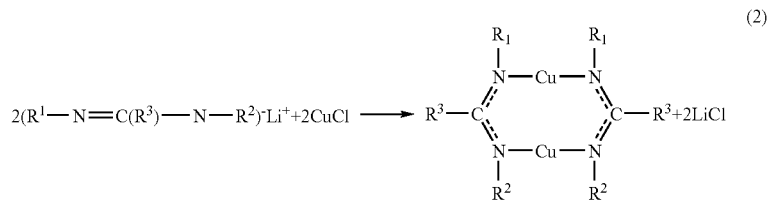

and wherein:
- $R^1$ and $R^2$ may be the same as or different from one another and each is independently selected from the group consisting of H, $C_1$–$C_6$ alkyl, $C_3$–$C_7$ cycloalkyl, aryl, and hydrocarbyl derivatives of silyl groups;
- $R^3$ is selected from the group consisting of H, $C_1$–$C_6$ alkyl, $C_3$–$C_7$ cycloalkyl, aryl, hydrocarbyl derivatives of silyl groups and $NR^4R^5$, where $R^4$ and $R^5$ may be the same as or different from one another and is independently selected from the group consisting of H, $C_1$–$C_6$ alkyl, $C_3$–$C_7$ cycloalkyl, aryl, and hydrocarbyl derivatives of silyl groups;
- with the provisos that:
  - when $R^1$ and $R^2$ are isopropyl groups or sec-butyl groups, $R^3$ is not a methyl group,
  - when $R^1$ and $R^2$ are p-tolyl groups or hydrogen, $R^3$ is not hydrogen, methyl or phenyl,
  - when $R^1$ and $R^2$ are phenyl groups, $R^3$ is not hydrogen, methyl or phenyl,
  - when $R^1$ and $R^2$ are trimethylsilyl groups, $R^3$ is not phenyl, and
  - when $R^1$ and $R^2$ are t-butyl groups or isopropyl groups, $R^3$ is not hydrogen.

9. The method of claim 8, wherein the copper precursor compound is selected from the group consisting of copper (I) 2-isopropyl-1,3-diisopropylamidinate and copper (I) 2-dimethylamine-1,3-diisopropylamidinate.

10. The method of claim 8, wherein $R^1$ and $R^2$ in the copper precursor compound are isopropyl groups.

* * * * *